(12) United States Patent
Logue (10) Patent No.: US 7,369,116 B2
(45) Date of Patent: May 6, 2008

(54) FOOT-OPERATED KEY PAD

(75) Inventor: Becky Logue, Meridian, ID (US)

(73) Assignee: Beckmer Products, Inc, Meridian, ID (US)

( * ) Notice: Subject to any disclaimer, the term of this patent is extended or adjusted under 35 U.S.C. 154(b) by 631 days.

(21) Appl. No.: 10/973,999

(22) Filed: Oct. 25, 2004

(65) Prior Publication Data
US 2005/0156878 A1      Jul. 21, 2005

Related U.S. Application Data

(60) Provisional application No. 60/513,929, filed on Oct. 23, 2003.

(51) Int. Cl.
*G09G 5/00* (2006.01)
(52) U.S. Cl. ........................ 345/156; 345/163
(58) Field of Classification Search ......... 345/156–168
See application file for complete search history.

(56) References Cited

U.S. PATENT DOCUMENTS

| | | | |
|---|---|---|---|
| 3,943,914 A | 3/1976 | Grenfell et al. .......... 128/2 S |
| 4,446,453 A | 5/1984 | Eenboom et al. ...... 340/286 M |
| 4,904,184 A | 2/1990 | Murphy et al. ................ 433/72 |
| 4,922,925 A * | 5/1990 | Crandall et al. ............. 600/595 |
| 5,144,753 A | 9/1992 | Murphy ....................... 33/514 |
| 5,197,487 A | 3/1993 | Ackerman et al. .......... 128/776 |
| 5,318,442 A | 6/1994 | Jeffcoat et al. ................ 433/72 |
| 5,334,997 A * | 8/1994 | Scallon ........................ 345/167 |
| 5,552,807 A | 9/1996 | Hayes et al. ................. 345/156 |
| 5,745,055 A | 4/1998 | Redlich et al. ................ 341/20 |
| 5,838,305 A * | 11/1998 | Bookstein .................... 345/163 |

(Continued)

FOREIGN PATENT DOCUMENTS

JP       09-114583        5/1997

(Continued)

OTHER PUBLICATIONS

Kinesis Programmable Foot Switch (PS/2 Version) User's Manual, Aug. 2000 Edition.

(Continued)

*Primary Examiner*—Ricardo Osorio
(74) *Attorney, Agent, or Firm*—Pedersen & Co., PLLC; Ken J. Pedersen; Barbara S. Pedersen (57) ABSTRACT

A foot operated data entry pad has a plurality of foot buttons. The foot buttons are used to enter data values—e.g., numbers or symbols separately or in combination. Each button is capable of entering different data values, preferably depending on the length of time that it is pressed or on the number of times that it is pressed in succession. A small controller may be included to allow the user to control the computer's pointer, allowing the user to switch between data entry fields, as with a mouse. An automated voice system, or other audible and/or visual indicator system, may also be included to help the user keep track of the data value as it changes and is entered. Various embodiments are capable of entering a variety of alphanumeric data rather than a simple binary-type data set, such as yes/no or on/off, or instructions, such as a joystick used with a flight simulator program. Multiple data entry pads may optionally be used in conjunction.

9 Claims, 8 Drawing Sheets

U.S. PATENT DOCUMENTS

| | | | |
|---|---|---|---|
| 5,886,685 A * | 3/1999 | Best | 345/163 |
| 5,889,510 A * | 3/1999 | Klarlund | 345/168 |
| 5,907,318 A * | 5/1999 | Medina | 345/163 |
| 5,910,139 A | 6/1999 | Cochran et al. | 606/1 |
| 5,993,209 A | 11/1999 | Matoba et al. | 433/72 |
| 6,091,402 A | 7/2000 | Howell | 345/157 |
| 6,470,222 B1 | 10/2002 | Davidson et al. | 700/2 |
| 6,600,477 B1 | 7/2003 | Howell | 345/157 |
| 6,611,250 B1 * | 8/2003 | Prince et al. | 345/163 |
| 6,714,188 B1 * | 3/2004 | Zebuhr et al. | 345/163 |
| 6,798,396 B2 * | 9/2004 | Gemunder et al. | 345/156 |
| 6,980,133 B2 * | 12/2005 | Foong | 341/20 |
| 7,062,365 B1 * | 6/2006 | Fei | 701/36 |
| 2002/0030661 A1 | 3/2002 | Gemunder et al. | 345/156 |

FOREIGN PATENT DOCUMENTS

JP      09-258887      10/1997

OTHER PUBLICATIONS

Kinesis Corporation Retail Price List, dated Aug. 22, 2003.

* cited by examiner

FOOT-OPERATED KEY PAD

This application claim priority of Provisional Application Ser. No. 60/513,929, filed Oct. 23, 2003, and entitled "Foot-Operated Data Entry Pad," which is hereby incorporated by reference.

BACKGROUND OF THE INVENTION

1. Field of the Invention

This invention relates to data entry devices for computers, and more particularly to foot-operated data entry pads.

2. Related Art

As an example of date entry, measuring and recording the depth of a periodontal pocket caused by a periodontal disease, such as gingivitis, is one of the most important diagnostic activities in dental care. There are many known apparatus for taking these measurements. Commonly, these measurements are entered into a digital database via a computer. However, conventionally, the dental worker taking the measurements has been unable to enter the data manually without having to put the measuring instruments down and move to a computer keyboard and/or mouse to record the measurements. Thus, the job is often performed by two or more workers. Thus, there is a need for such a data entry system that can be operated easily without the use of hands.

For example, Grenfell, et al. (U.S. Pat. No. 3,943,914) attaches a foot pedal to an automatic probe used to measure gingival sulcus. The user positions the probe for measurement, and then activates the foot pedal. This triggers the automatic probe to take a depth measurement and transmit the result to the data recording system. Other devices, such as Murphy, et al. (U.S. Pat. No. 4,904,184); Murphy (U.S. Pat. No. 5,144,753); Jeffcoat (U.S. Pat. No. 5,318,442); and Matoba, et al. (U.S. Pat. No. 5,993,209) have similarly used a footpad to instruct an instrument to take a measurement and transmit the reading to a data recording system.

Ackerman, et al. (U.S. Pat. No. 5,197,487) uses a foot activated switch to switch between different modes of operation for analyzing and organizing data from a probe. However, the switch is not used to actually enter any data.

Eenboom, et al. (U.S. Pat. No. 4,446,453) discloses a foot pad capable of very simple data entry. This device is capable of entering a bare yes/no response for the presence of plaque on a patient's teeth. Matoba, et al. (U.S. Pat. No. 5,993,209) also teaches a device that also is used to indicate whether plaque is present on a patient's teeth.

None of these devices are capable of entering information beyond a simple binary data set—e.g., yes or no, either/or, or on or off.

Also, there are references which disclose foot-operated controls for computers. For example, Hayes, et al. (U.S. Pat. No. 5,552,807) discloses foot pedal controls for both flying and driving games. Also, Bookstein (U.S. Pat. No. 5,838,305) and Howell (U.S. Pat. No. 6,091,402) discloses foot-operated control of the position and movement of the computer's cursor. Also, Klarlund (U.S. Pat. No. 5,889,510) discloses a foot-operated keyboard with two arrays of switches—one in the toe-resting region, and one in the heel-resting region. Also Cochran, et al. (U.S. Pat. No. 5,910,139) and Davidson, et al. (U.S. Pat. No. 6,470,222) discloses remote control of surgical and/or dental instruments with a foot pedal controller. However, there is still a need for a foot-operated data entry system capable of allowing entry of a wider range of data, such as numeric or alphanumeric information.

SUMMARY OF THE INVENTION

The invention is a foot operated data entry pad designed for entering informational data over a desired range for recordation. In a preferred embodiment, one or more foot buttons are provided. Data is entered by pressing the appropriate foot button. Foot buttons are arranged in a spaced-apart, generally radial planar pattern, distanced about ⅔ of an average foot length (about 5-10 inches) from a heel rest region. Optionally, the heel rest region may also comprise another switch. Preferably, different discreet values may be entered by pressing the same foot button different lengths of time or, in an alternative embodiment, by repeatedly pressing it.

Additionally, in the preferred embodiment, a joystick-type or other controller is used to control the computer's pointer, as it is often necessary to move a cursor between data entry fields. Preferably, the data entry pad will work seamlessly with existing hardware and software by mimicking the mouse and keyboard—i.e., the computer receives and processes input from the data entry pad as signals from the mouse and keyboard.

Optionally, the preferred embodiment also includes an automated voice system that announces entered values and/or the current value to be entered if the user releases a foot button or otherwise ceases to cause the data value to increment.

Alternatively, the controller and data entry functions may be separated into two separate devices, or the controller function may be omitted. Multiple data entry pads may also be used together to increase the capacity of the system.

DETAILED DESCRIPTION OF THE INVENTION

Figure 7:
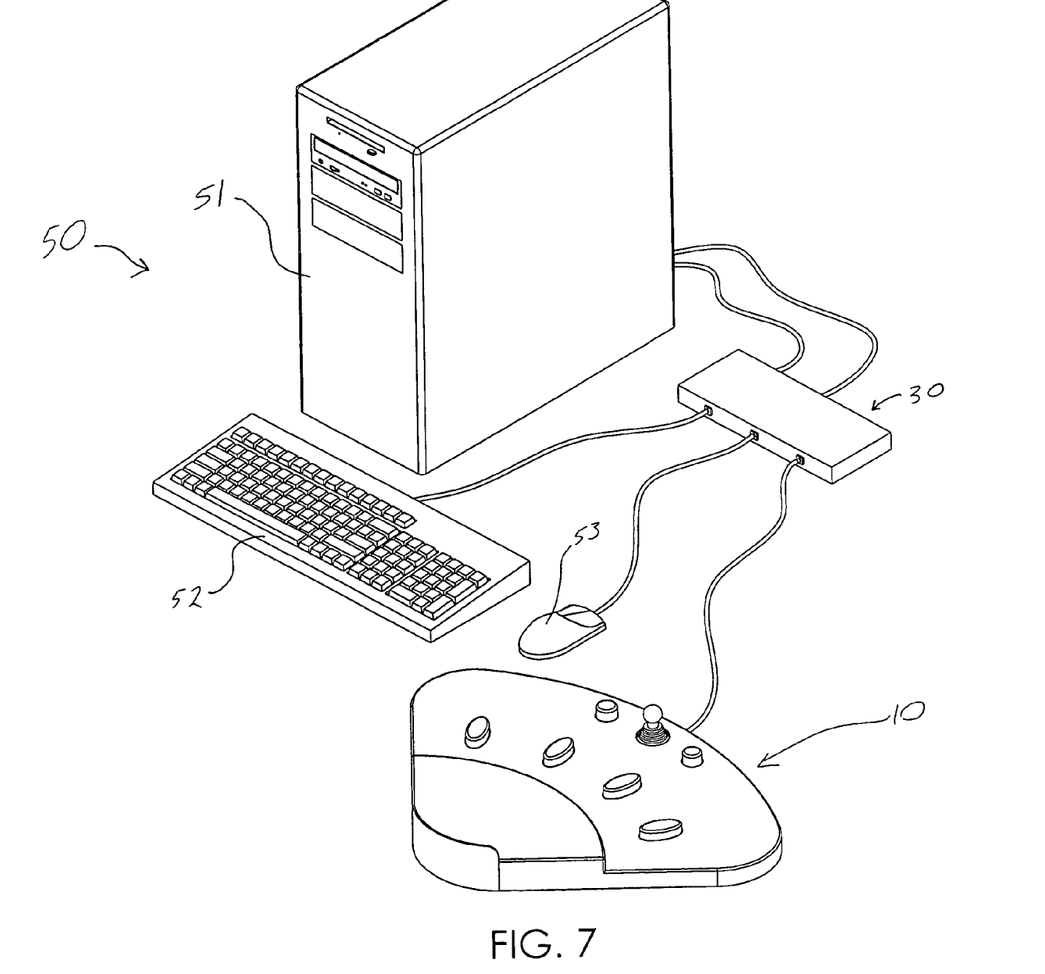
FIG. 7 is a perspective view of the embodiment of FIGS. 1 and 2 of the invention in connection with a computer system.

Referring to the Figures, there are shown several, but not all, embodiments of the invented foot operated data entry pad. As illustrated in FIG. 7, the invented data entry pad integrates with a larger system that preferably includes a computer, with its usual accessories—i.e., mouse, keyboard, and monitor (not shown)—and preferably an adapter, called a multiplexer, that allows the footpad to interface seamlessly with existing computer hardware and software. The preferred multiplexer connects to the data entry pad and the computer's other input devices—i.e., mouse and keyboard—and controls their respective signals so that the computer perceives all input as though it came only from the mouse or keyboard. Thus, with the preferred embodiment, there is no need for additional or new software and the data entry pad can be integrated easily with existing systems.

The term "data" is used herein to refer to information to be stored for later retrieval. In the preferred embodiment, the data is an integer referring to the depth of a periodontal pocket, measured in millimeters. However, the term may include any information represented by numbers or other symbols, such as letters, that is stored for later review. The term "data" does not refer to instructions, such as sent by a controller for a pointer or program operation, such as a video game control. "Data" also does not refer for this invention to simple binary data sets—i.e., where one of two options, such as yes or no, red or green, or on and off is the only correct choice.

Figure 1:
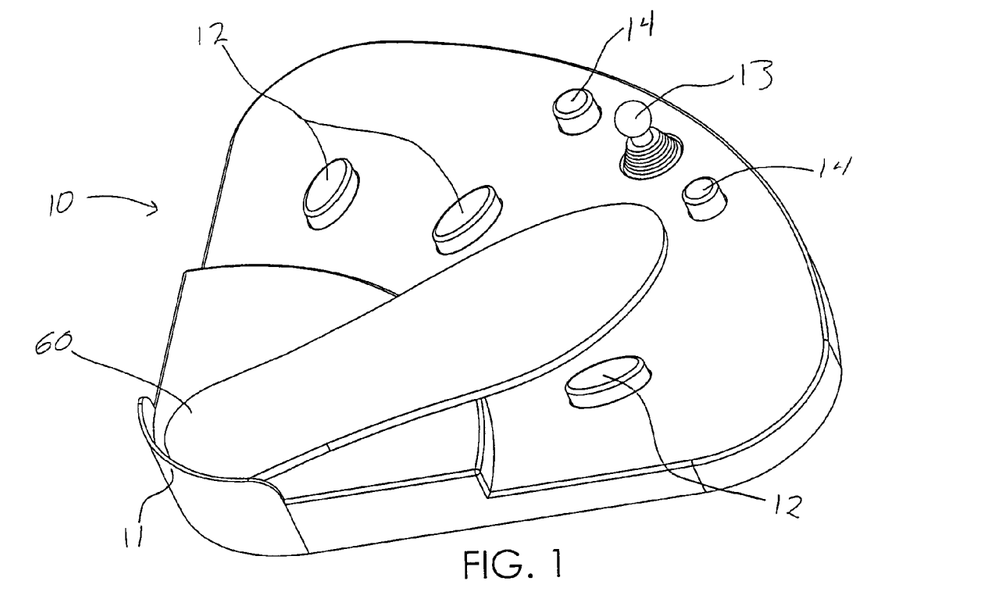
FIG. 1 is a perspective view of the preferred embodiment of the invented foot-operated data entry pad with a schematic shoe sole included for illustrative purposes.
Figure 2:
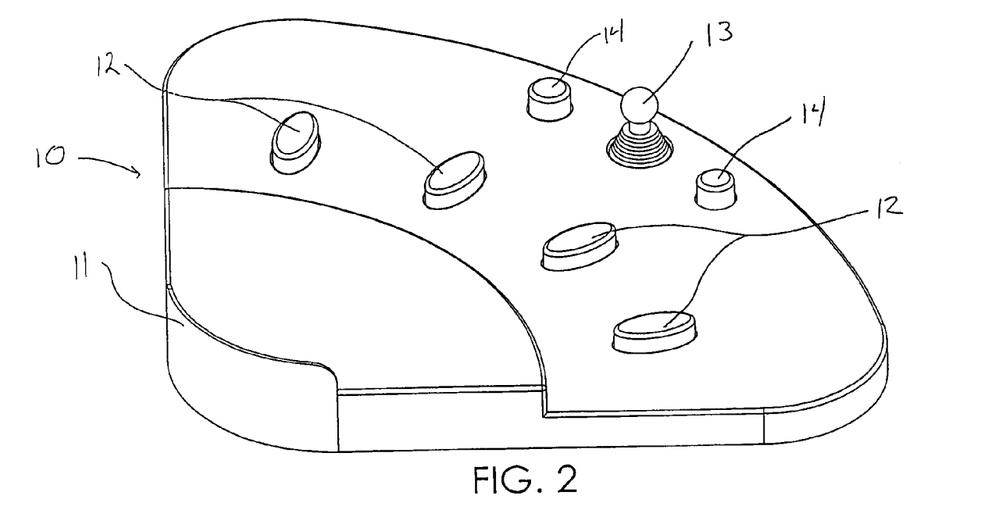
FIG. 2 is a perspective view from a slightly different angle of the embodiment of FIG. 1 with the schematic shoe sole removed.

Referring to FIGS. 1 and 2, the preferred embodiment of the invented data entry pad 10 comprises a heel support 11, plurality of foot buttons 12, controller 13, and one or more controller buttons 14. The user places the heel of the foot on heel support 11 and pivots the foot on that point to reach each of the foot 12 buttons. The foot buttons 12 are arranged in a spaced-apart, generally radial planar pattern. This way, the data entry pad operator may access each of the buttons singly, without disturbing the other buttons. Also, this way the operator may access each of the buttons by simply rotating the foot about the heel which is in the heel support area 11. Typically, the foot buttons 12 are spaced-apart about 1½-5½ inches. Also typically, the foot buttons are distanced about ⅔ of an average foot length (about 5-10 inches) from the center of heel support area 11. The foot button radial pattern may extend in an expanding pie shape out from the heel support area 11 from about 30° to abut 150°, depending upon the number of buttons in the pattern. The buttons may be present in one or more rows. When there are multiple rows of buttons, preferably they are staggered to maximize distance between the buttons. As described in more detail below, the data value sent to the computer preferably depends on which foot button 12 is pressed and also on the number of times, or the length of time, that it is pressed. As illustrated by the inclusion of foot sole 60 in FIG. 1, controller 13 and controller buttons 14 are preferably beyond the reach of the user's foot when the heel is touching heel support 11 to prevent accidental activation of controller 13 and/or controller buttons 14. Other foot buttons 12 could be added to the data entry pad to mimic, for example, the shift key, control key, or mouse buttons, etc. Alternatively, a controller button 14 may be replaced by designing heel support 11 to register and transmit a signal—e.g., either mouse button signal—when heel support 11 is pressed down by the user's heel. In some applications, one or both of controller buttons 14 could be omitted.

The preferred foot buttons 12 are Hall-effect sensors. They are preferably narrower than a foot to allow them to be closer together and position-error tolerant—if foot buttons 12 were as wide as a foot, the user would have to move his foot at least one foot-width between foot buttons 12, and foot buttons 12 would have to be spaced at least one foot-width apart. If foot buttons 12 are, as in the preferred embodiment, only one-half inch in diameter, then when the user is pressing one foot button 12, the other foot buttons 12 can be close to the user's foot on either side. Therefore, the preferred space between foot buttons 12 is one-half foot-width plus one-quarter inch, about 3 inches. As a result, the user only has to rotate the foot by this reduced pitch. This gives more foot buttons 12 for the same ankle rotation, or reduces the amount of ankle rotation. Alternatively, heel support 11 could be designed to allow the user's heel to move laterally, by sliding or lifting it, to reach foot buttons 12 while reducing or eliminating the need for ankle rotation.

Each foot pedal key can be used for multiple purposes by double-clicking or by holding down for an extended time. For example, if the "one" button is held for one second or longer, it becomes a "five". Voice feedback can say "one" if the pedal is released before one second, and it can say "five" at the one second point so that the user knows to release the button. In the case of two functions per button, the data can be transmitted either at the transition time or upon pedal release. Additional functions can be achieved by holding the button longer still. Also, mouse functions and keyboard functions can be mixed. For example, holding the "four" button for one second makes it an "eight" button, but holding it for three seconds makes it a mouse "right click" button. If there are three or more functions per pedal, the data cannot be transmitted until the pedal is released. If there are three or more functions, the voice feedback can simply announce the next functional level or can insert a substitute word such as "rather" before the function or data name (e.g., "rather, nine").

Figure 8:
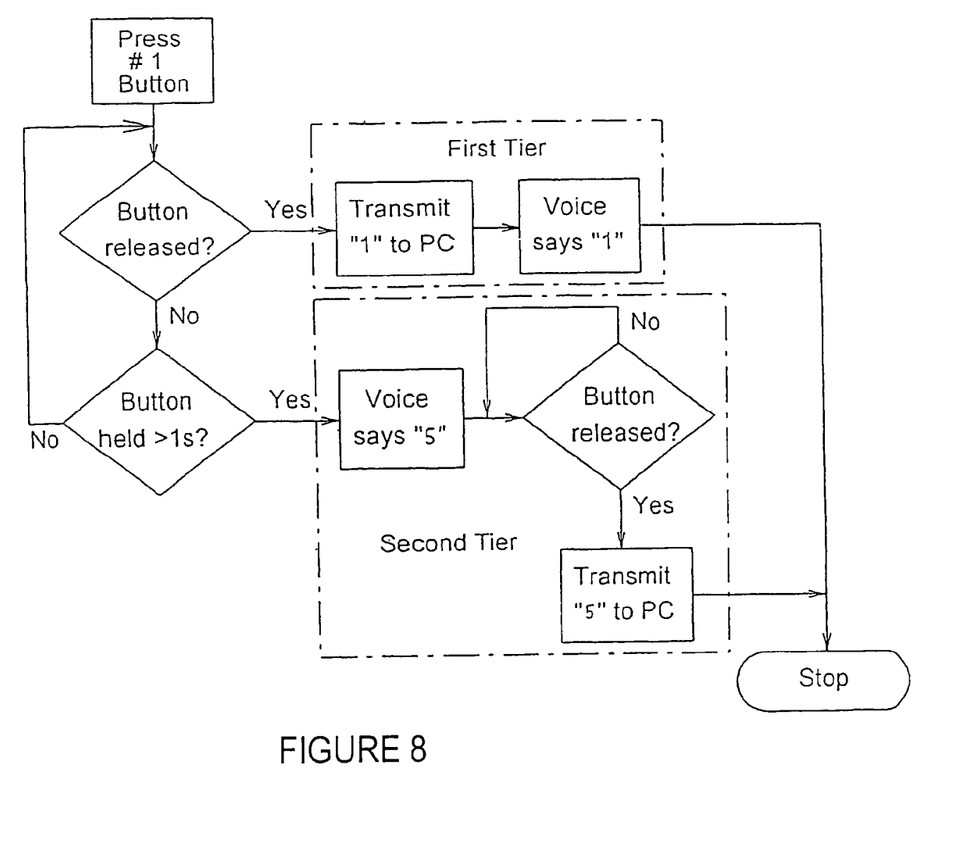
FIG. 8 is a logical flow diagram illustrating the foot button operation of the preferred embodiment of the invention.

Referring to FIG. 8, the operation of the foot buttons in the preferred embodiment for dental application is illustrated. The first foot button 12, with an initial data value of 1, is used for illustrative purposes. Preferably, each foot button 12 is capable of entering more than one data value. This is preferably accomplished by making the data value entered dependent on which foot button 12 is pressed and on how often or on how long it is continuously pressed.

To enter a given data value, the user presses the appropriate foot button 12, but the data value is preferably sent to computer 51 only after foot button 12 is released. For example, if the chosen foot button 12 is released before a set time period—preferably one second—has passed, the initial data value associated with the chosen foot button 12 is transmitted to an automatic voice system, which announces the data value, and to the computer system for recording. As illustrated in FIG. 8, the resulting data value would be 1. The other three foot buttons 12 have initial data values of 2, 3, and 4. If the foot button is not released in less than the set period of time—i.e., one second for the preferred embodiment—the initial data value is increased by four, and the new value is sent to the automated voice system for announcement, but not to the computer system. The data value is sent to the computer system once the foot button is released. Optionally, the data value could be reannounced as entered at this point.

In the preferred embodiment, each foot button 12 is associated with two data values—e.g., 1 and 5 for the first button, as illustrated in FIG. 8—covering the integers from one to eight, inclusive. Although the preferred embodiment permits entry of only a small range of data values, any appropriate data values can be chosen as the upper and lower limits, including no upper limit or infinity—or an upper limit, and no lower limit with descending rather than ascending numbers. Thus, continuing to hold foot button 12, in this example, could result in the data value increasing by four—i.e., to 9, 13, etc.—infinitely or, preferably, to any appropriate maximum for a given application. Also, the increment between data values need not be one, or any other value, but can be set at any appropriate amount for a given application. Besides,

[1] This routine is for each button. Any number of buttons can be used.

[2] Digit entry is shown here, but entry can be any digit, character, symbol, word, phrase, etc., that is desired to be entered into the PC.

[3] Wait times between increments can be set to any value to optimize usability.

[4] More tiers of increments can be added. The voice says something new after each increment time period, but the entry is not transmitted until the button is released.

Figure 9:
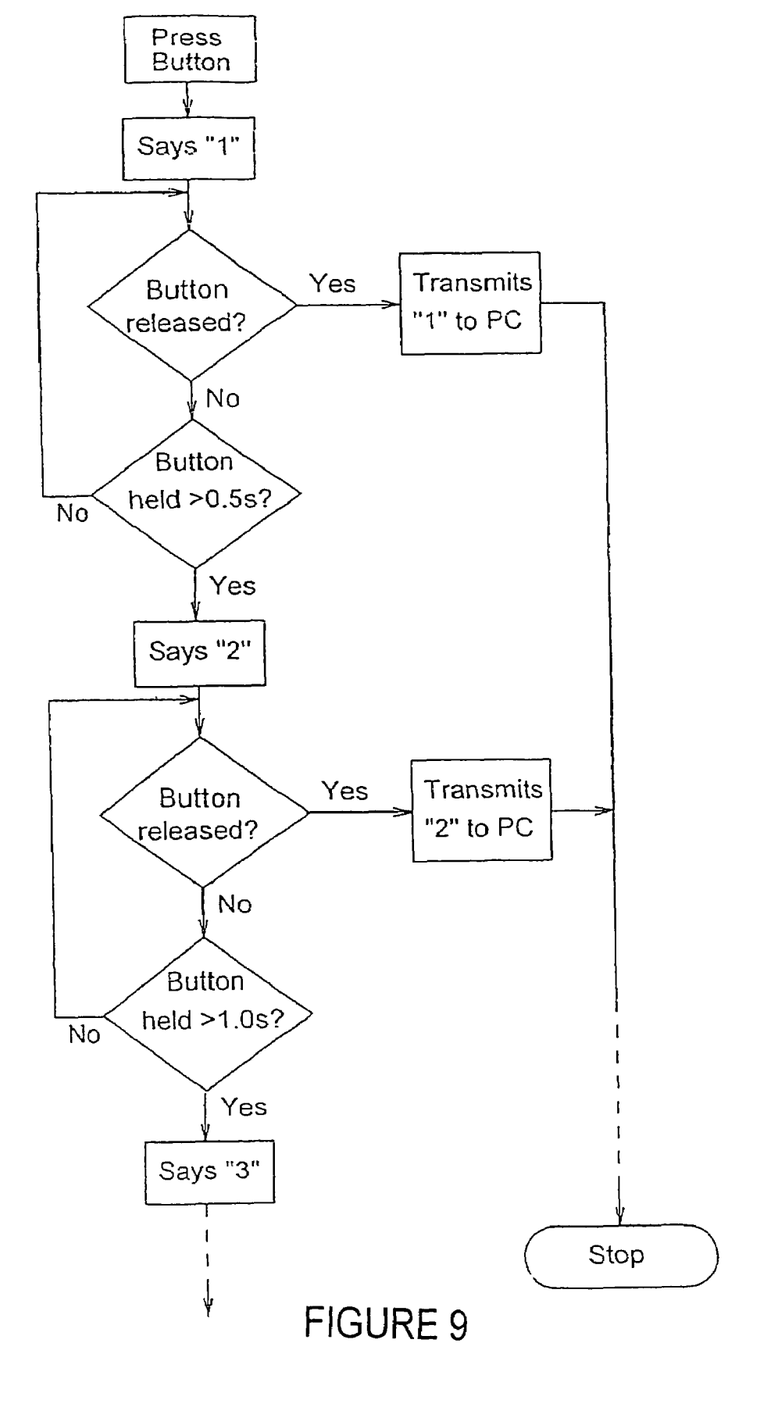
FIG. 9 is a logical flow diagram illustrating the foot button operation of an alternative embodiment of the invention.

Referring to FIG. 9, the operation of the foot buttons in one alternative embodiment is illustrated. In this example, the initial data value is 1 and increases by increments of 1. This could be the case where there is only one foot button 12, where the initial data values for other foot buttons 12 are non-integers—e.g., 1.25, 1.5, and 1.75—or where other foot buttons 12 operate for number ranges wholly greater or lesser than those for the foot button 12 in the example—e.g., one button could be used to enter values from 1 to 10, another to enter values from 11 to 20, and so on. In the embodiment of FIG. 9, the button is held down until the desired entry is heard. Then upon releasing the button, the entry is transmitted to the PC. The set time period after which the data value is increased is 0.5 seconds rather than the 1.0 second of the preferred embodiment—any time period can be chosen, but it should preferably be long enough for the user to release the foot button 12 before the data value changes without being so long as to make the device unproductively slow. No limit to the values that can be entered is shown in the embodiment of FIG. 9, but one could be added. Likewise, any increment between data values may be chosen, depending on the needs of any given application. When the chosen foot button 12 is pressed, the initial data value is sent to the automated voice system and announced. Each time the data value changes, it is sent to the automated voice system and announced. The data value is sent to the computer only after the chosen foot button 12 is released. Optionally, this data value could be re-sent to the automated voice system and reannounced as entered.

Figure 10:
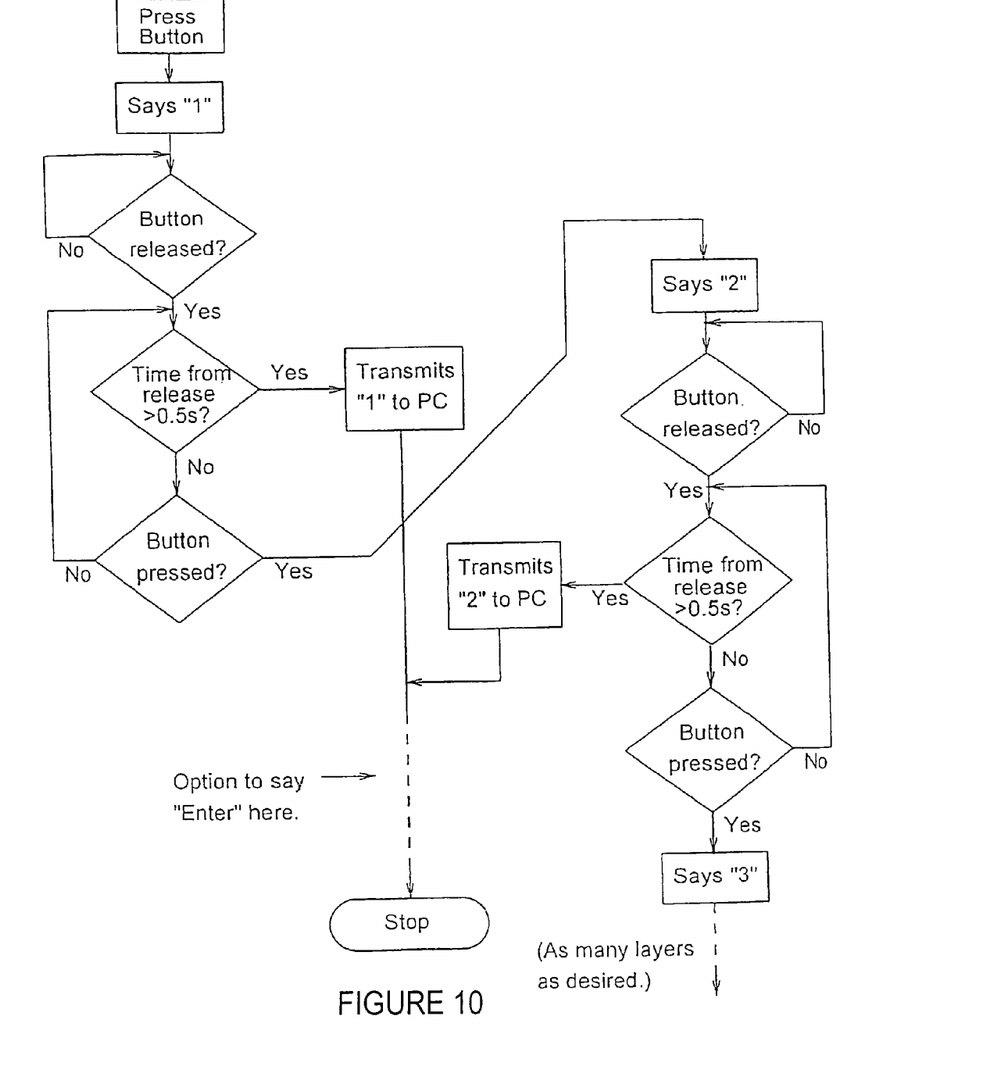
FIG. 10 is a logical flow diagram illustrating the foot button operation of another alternative embodiment of the invention.

Referring to FIG. 10, the operation of the foot buttons in another alternative embodiment is illustrated. In this variation, the button is pressed and released until the desired entry is heard. Then when the button has been released for over ½ second, the entry is transmitted to the PC. In this case, a chosen foot button 12 is pressed, released, and re-pressed within a set period of time to enter a data value. Like the embodiment of FIG. 9, the initial data value is one and the increment between data values for a foot button 12 is 1. When the appropriate foot button 12 is pressed, the associated initial data value is announced. When the button is released, the device waits a preset period of time—in this case, 0.5 seconds—to see whether the button is re-pressed. If the button is not re-pressed, the data value is sent to the computer system. If the button is re-pressed during the preset time period, the data value is incremented and the new value announced. This process is repeated with increasing data values until the button is not re-pressed within the preset time period. At that point, the last data value is sent to the computer system. As with the other embodiments, limits on the range or data values enterable may be imposed for convenience, but are not required. Likewise, the increment between data values may be set at any amount appropriate for a given application.

The techniques discussed above relating to FIGS. 8-10 with timing or repeat features amount to a code of actuation for the foot buttons(s).

Most people are not able to accomplish fine motor movements with their feet. Therefore, it is a further aspect of this invention to develop a joystick which can precisely position a cursor on a computer screen, but which doesn't require accurate foot movements. The joystick is digital, meaning that it is on or off, rather than proportional. If it is pressed up, the cursor begins moving up. If it is released, the cursor stops. The joystick does not control cursor position or cursor speed. It only controls approximate direction of travel. In the preferred embodiment, the joystick will only move in eight discrete directions (up, right, 45 degrees up and right, etc.). Alternatively, the joystick could be made to move the cursor in any direction. The cursor can move at a constant speed, but in the preferred embodiment, it starts out slowly and then increases its speed more as the joystick is pressed longer. In this way, quick on-and-off, in a form of "dithering", motions can achieve very fine cursor manipulation, while pressing the joystick longer can cause the cursor to traverse the screen in a reasonable amount of time. Although applicable to foot operation, this feature of the invention can also be used for a hand-operated device for those who cannot perform fine-motor movements with their hands.

In the preferred embodiment, the user is able to perform any point-and-click operations that the user's software includes with controller 13 and one or more controller buttons 14. The preferred controller 13 is a short joystick. Alternatively, a rocking panel may be used. Controller 13 controls the cursor by causing it to move in a chosen direction. Optionally, the speed of the cursor may be adjustable and/or increasing the longer controller 13 is held off-center. Preferably, one or more controller buttons 14 are placed to one or both sides of controller 14. Alternatively, a controller button 14 may placed in the center of the controller so that when the controller is released, the button is released and activated to send a computer mouse left or right button signal to computer 51. Because controller 13 and controller buttons 14 are placed beyond the reach of the user's foot when the foot is contacting heel support 11, the user moves his foot forward from heel support 11 to operate controller 13 and controller buttons 14. In the preferred embodiment, controller buttons 14 mimic the functions of the left and/or right mouse buttons.

Digits or other data can be input using one of several foot pedals or buttons. Alternatively, the heel or foot can rest on a pivoting platform, pad, cradle, or footrest. When the pivoting member rotates about an axis roughly parallel with the ankle, its rotational position may be sensed by optical, mechanical, Hall-effect, proximity, or other means and is interpreted as being in one of N positions. For example, four discrete positions can be detected using only two discrete detectors. If the detectors are optical, then an interrupter, cam, or reflector plate could trigger only the first detector, both detectors, only the second detector, or no detectors. Depending upon which of these four combinations is detected, the correct data is selected for transmission. Then the data can be entered, for example, by rocking the pivoting foot device about a second axis roughly perpendicular to the first. When the foot device rocks, it detects the rotational motion. Alternatively, the foot could rock forward (whether the foot device pivots or is shaped to allow the foot to rock) and touch a button or bar or be sensed in another way to activate a switch, and initiate an entry.

Figure 3:
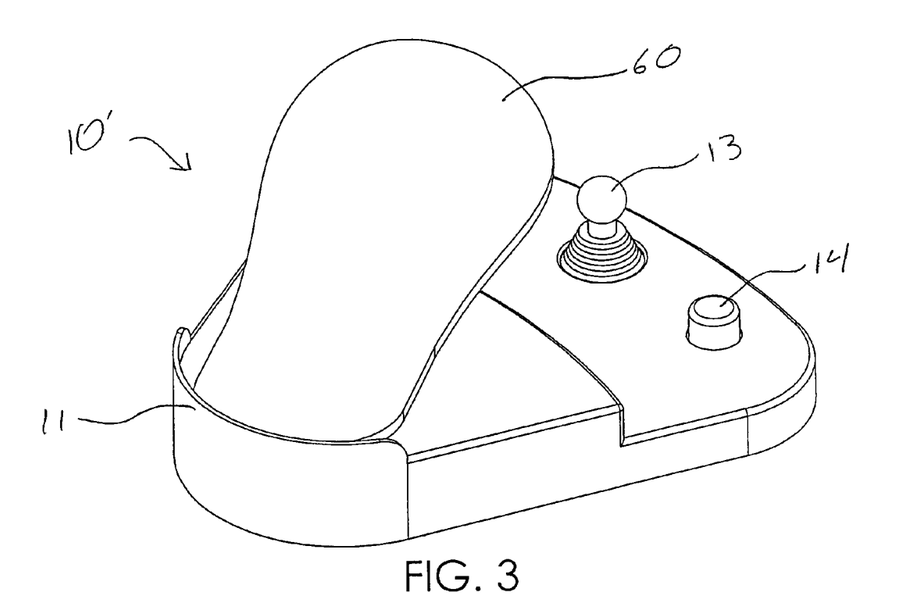
FIG. 3 is a perspective view of one alternative embodiment of the invented data entry pad with a schematic shoe sole included for illustrative purposes.
Figure 4:
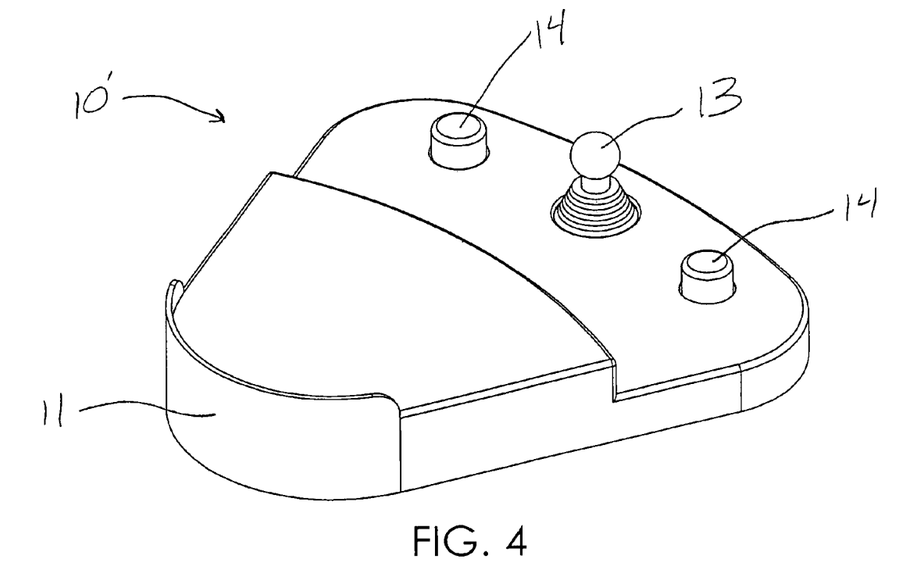
FIG. 4 is a perspective view of the embodiment of FIG. 3 with the schematic shoe sole removed.

Referring to FIGS. 3 and 4, one alternative embodiment is data entry pad 10' with only controller 13 and controller buttons 14 is shown. Controller 13 and controller buttons 14 function as in the preferred embodiment, described above, except that the user can operate controller 13 and controller buttons 14 without moving his feet forward from heel support 11, as illustrated by foot sole 60 in FIG. 3. In this embodiment, there is no foot button 12. However, controller buttons 13 and 14 may be actuated with a simple heel rotation before applying pressure on buttons 13 and 14 with the toes or ball of the foot.

Figure 5:
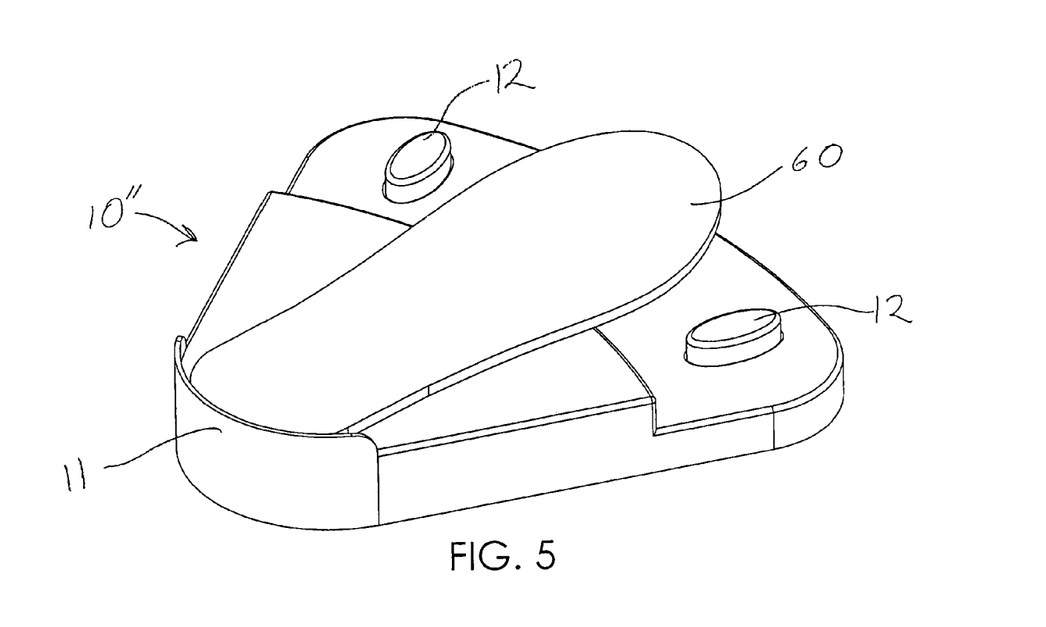
FIG. 5 is a perspective view of one alternative embodiment of the invented data entry pad with a schematic shoe sole included for illustrative purposes.
Figure 6:
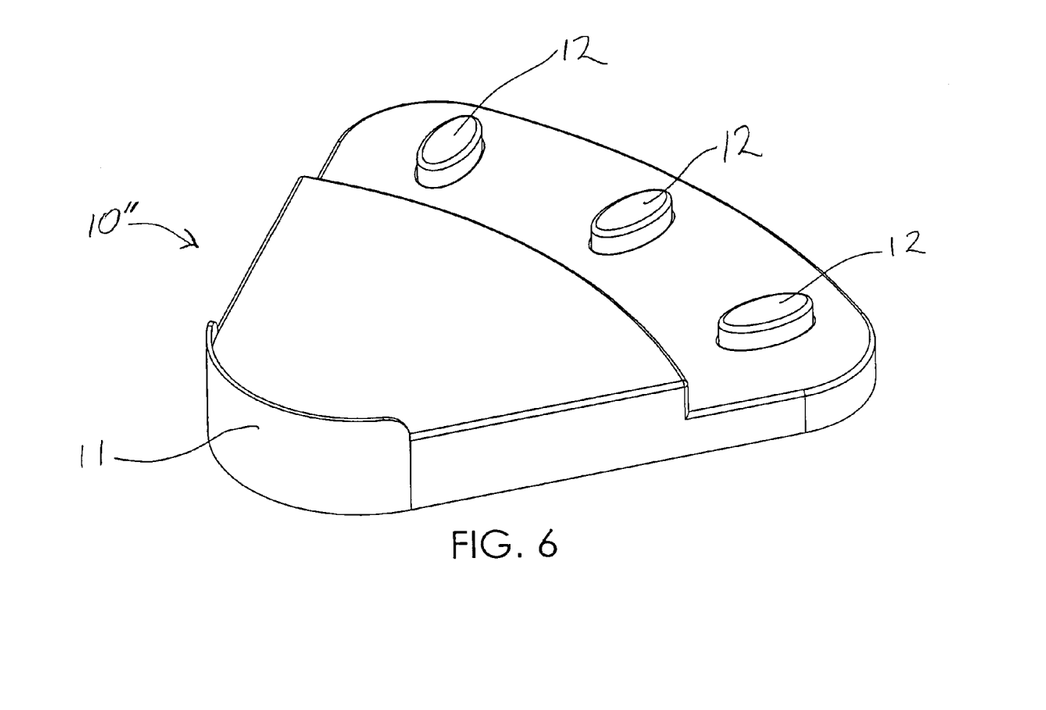
FIG. 6 is a perspective view of the embodiment of FIG. 5 with the schematic shoe sole removed.

Moving on to FIGS. 5 and 6, an alternative embodiment of data entry pad 10" is shown. It is shown with three foot buttons 12, and with no controller or controller buttons. Foot buttons 12 function as in the preferred embodiment, described above, except that the interval between data points is three rather than four because of the number of foot buttons 12 included. Preferably, the two embodiments in FIGS. 3-6 are used in conjunction, giving the user all the capabilities of the preferred embodiment. The user may operate each device with a separate foot or may switch his foot back and forth, as the user prefers.

Referring to FIG. 7, the preferred embodiment of data entry pad 10 is illustrated connected to a typical computer system 50 used for data entry. Data entry pad 10 is connected to multiplexer 30. Mouse 53 and keyboard 52 are also connected to multiplexer 30. Multiplexer 30 is connected to computer tower 51 via two cords, which connect to the computer's mouse and keyboard ports (not shown). Multiplexer 30 receives signals from keyboard 52, mouse 53, and data entry pad 10. Signals from data entry pad 10 are identified as mouse-type or keyboard-type signals. Signals from all input devices are prioritized and sent to the appropriate computer port—i.e., the mouse or keyboard port. Although the preferred embodiment is shown connected to computer system 50 via wires, any or all of the connections may be wireless using any wireless technology—e.g., methods used for a wireless mouse or wireless laptop connections.

Ideally, the data input device should be connected to the computer in a way that is invisible to the application software. Connecting to the serial port would require modifying application software to look for data input at that port. Connecting to a USB port is simple, but in some cases will require installing special driver software. This is a reasonable approach, as it will be invisible to the application software that is manipulating or storing the data. The preferred embodiment is to input data and cursor movement through the mouse and keyboard PS/2 ports. This is where the computer and application software receive their data and cursor instructions.

Unplugging the keyboard and mouse to connect the foot pedal, then changing back for hand-typing additional data would be unacceptable, especially because the computer must be turned off to plug and unplug devices to the PS/2 ports. Therefore, a means to mix or multiplex the signals from mouse and joystick and mix the signals from the keyboard and foot pedal is required.

Figure 11:
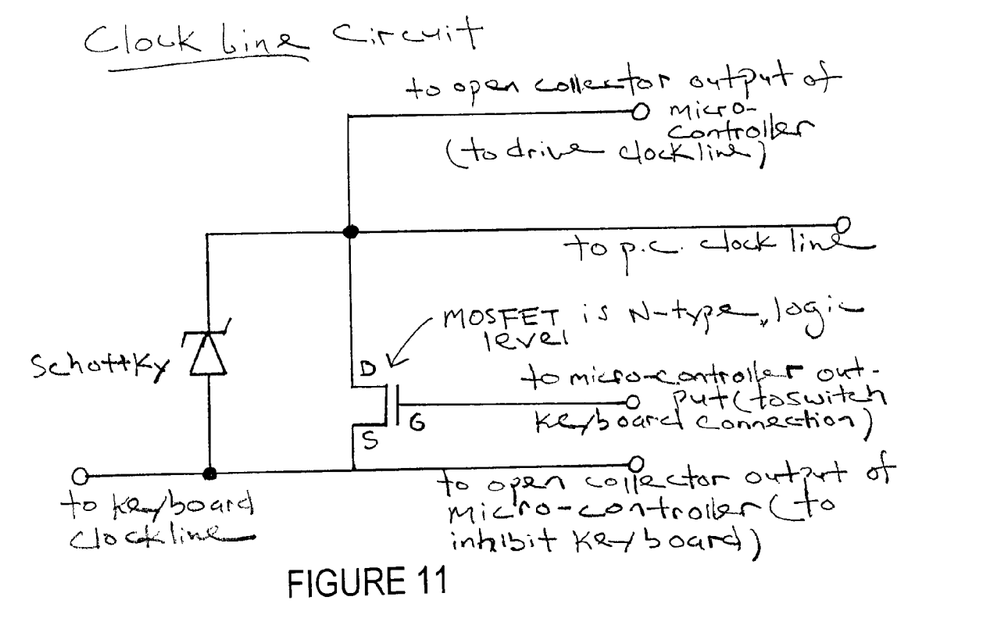
FIG. 11 is a schematic wiring diagram of the clock line circuit for the multiplexer of the preferred embodiment of the invention.
Figure 12:
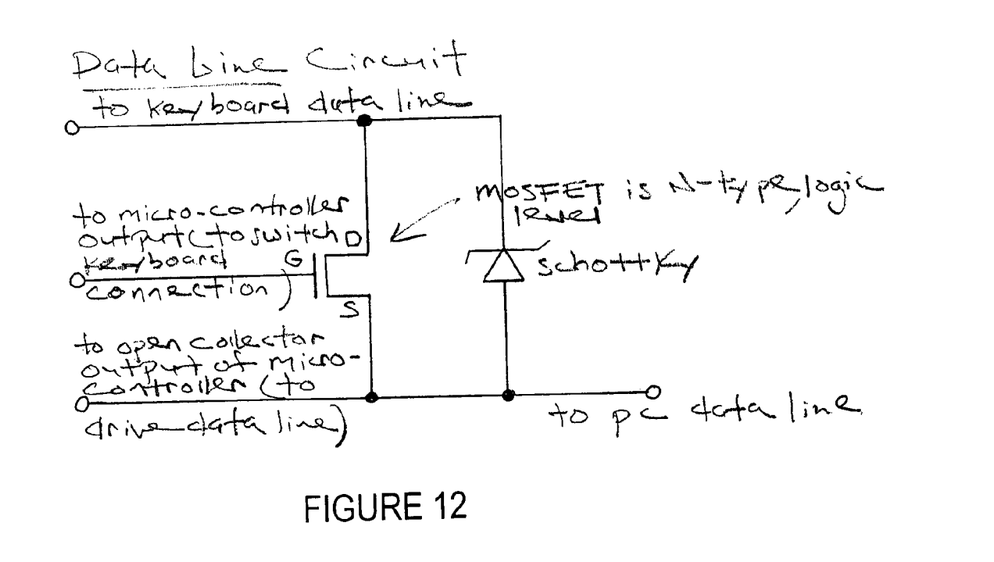
FIG. 12 is a schematic wiring diagram of the data line circuit for the multiplexer of the preferred embodiment of the invention.

There are several ways to accomplish this multiplexing or "wye" connection.

a) An 8-pole, double throw switch could connect the four mouse lines and four keyboard lines from the computer to either the keyboard and mouse, or to the foot pedal and joystick device.

b) All the ground/common/negative lines could be permanently connected together and a 6-pole, double throw switch can be used to connect the remaining lines.

c) Adding a large capacitor between power and ground lines on the computer side of these switches could minimize the effects of hot switching.

d) The ground/common/negative lines could be permanently connected together, the power lines could be permanently connected together, and then a 4-pole, double throw switch would connect the two data lines and two clock lines. This requires that power consumption of the foot pedal device plus keyboard and mouse to be low enough to fit within the PS/2 specification for computer-supplied power.

e) Same as (d) above, but power is augmented with a wall transformer. For example, if optical detectors are used, their LEDs could be powered by an auxiliary power source.

f) The switches in the scenarios above could be replaced by solid-state switching devices or relays.

g) The scenarios above all require the user to flip a switch to change between devices. A smart technique would allow input to be received from any device without user intervention. The user should be allowed to seamlessly switch from keyboard to foot pedal and mouse to joystick, and vice-versa. One way to accomplish this is to use one or two micro-controllers to manage the communication between the peripheral devices and the PC. In PS/2 communication, the PC is the host. If the micro-controller acted like a host to the keyboard and mouse it could receive their input data and could also receive data from the foot pedal. Then the micro-controller could act like a slave to the PC, looking like a keyboard and mouse. In this way it could input the data from all devices while looking like one keyboard and one mouse. Communication between the foot pedal and micro-controller could be PS/2, I$^2$C, or any other proprietary or standard protocol, or the foot pedal sensors could input directly to the micro-controller. The micro-controller could pass signals in near real time, mimicking the clock and data signals from a peripheral or PC, or it could process one data byte or packet at a time before relaying it to the PC. While the micro-controller is sending data from the foot pedal to the PC, it can pull the keyboard clock line low to inhibit the keyboard. The keyboard will buffer any data it has to send until the clock line goes high. In this way, data from the keyboard, mouse and foot pedal can be inter-mixed (multiplexed) to be fed to the PC in the order it is input by users, and at a speed still exceeding the user's ability to enter the data. Data from all devices gets processed and the computer cannot tell whether a cursor movement was initiated by a mouse or joystick, or whether data is coming from a keyboard or foot pedal.

h) A micro-controller between a keyboard and PC or between a mouse and PC will cause signal delays which could potentially result in malfunction. Therefore, the preferred embodiment uses MOSFETs and diodes to connect and disconnect the signals between these devices. See the FIGS. 11 and 12 following. The clock and data lines of a PS/2 port are open collector; they float high with the help of a resistor and can be pulled low by either the PC or peripheral device (keyboard or mouse). When the devices are connected (MOSFETs are turned on by pulling gates high), the keyboard or mouse can communicate directly with the PC and there is essentially no signal delay. The device pulls the clock line low through the MOSFET and pulls the data line low through the diode. The PC pulls the device clock line low through the diode and pulls the data line low through the MOSFET. When the MOSFETs are turned off (gates are pulled low), the device is disconnected, the device is inhibited by pulling its clock line low, and the clock and data lines on the PC side can be manipulated by the micro-controller to communicate foot pedal information to the PC. In this disconnected state, the device clock line is already low, so clock transitions on the PC side will not be changing the clock line through the diode, but the diode allows the line to go high. When the device is inhibited, it will let its data line float high. The data line on the PC line can go high and low while being isolated from the device by the diode.

i) A further aspect of the invention is that the micro-controller can monitor communication between a device and the PC. One use of this is to determine which kind of mouse to emulate. The PC queries the mouse at start-up to determine which kind of mouse it is, and therefore knows how to read and interpret the mouse information it receives. If the micro-controller monitors this communication, it can then emulate that same kind of mouse in its communication. This allows the multiplexer to be universal in application with any standard PS/2 mouse.

j) Although less user friendly, a simpler implementation to select between the most common mouse types is to use configuration switches set at the factory or by the user. For example, one setting would cause three-byte mouse packets to be transmitted and another setting would cause four-byte mouse packets to be transmitted.

k) Watching PC-to-mouse communication also allows the micro-controller to capture and emulate the same resolution, scaling, and other factors relevant to cursor movement.

m) The keyboard or mouse can be kept in an inhibited state for several milliseconds after the micro-controller transmits a foot pedal command to see if the PC sends a "resend" command. If so, the micro-controller must retransmit its last data.

n) If the voltage drop across the Schottky diode is problematic, then an open-collector op-amp/comparator circuit can be used as a buffer to follow signals to their low-level state. A rail-to-rail op-amp will achieve an almost perfect zero voltage.

o) Many N-type MOSFETs have a diode between their source and drain. If their voltage drop is not a problem, then it is possible to implement the circuit without the external diode shown in the sketch.

Although the invention is shown at one size, various methods may be used to accommodate various sizes of feet. For example, models may be made in different sizes. More preferably, heel support 11 may be made adjustable so that it may be moved forward or backward—i.e., along a line passing through the center of heel support 11 and controller 13. The adjustment method may be continuous—i.e., may be set at any point—or have discreet setting—i.e., a plurality of locking points.

The preferred embodiment is designed for entering periodontal data—e.g., the depth of gingival sulcus. Based on the needs of this application, the preferred embodiment has four foot buttons and is capable of entering data values from one to eight, inclusive. For example, the user would take a measurement with an instrument—e.g., a 3. The third foot button of the data entry pad is then pressed and promptly released to enter this value. If necessary, the controller is used to move a cursor, or similar pointer, to another data entry field on the screen. The next measurement is taken and recorded—e.g., a 5. The first foot button of the data entry pad is pressed and held until the data value is incremented to 5. It is then released and the data value is recorded. This process continues until all necessary measurements are taken and recorded. In cases wherein the measurements are always taken in the same order, and the software is adapted to receive this order of measurements, there may be no need for controller use between the measurements.

Although the invention has been described as applied to recording the depths of gingival sulcus, it may be used to enter data for any purpose without exceeding the scope of the invention.

Although the invention has been described as including one data entry pad, a second pad could be added. The user could use both feet and the number of foot buttons that could be included would be expanded. Also, the invented foot operated data entry pad may be adapted to input other than numerical data. For example, by adding foot buttons and using two data entry pads, the invention could be used to enter other types of data, such as alphanumeric symbols, words, or phrases. Although the embodiments have been described as having four foot buttons, it is not limited to any particular number of foot buttons and may be adapted to enter any numerical range just as a standard number pad on a keyboard—i.e., the data entry pad enters digits 0 through 9, with a decimal point as needed, to input data values.

The invention preferably includes an automated voice system that announces data values at various points in the system's operation. Any conventional automated voice system may be used, and the voice may be broadcast from a built-in speaker(s) or over the computer system's audio system—e.g., by adding a connection to the computer's microphone jack. Alternatively, a simpler system, such as an audible beep, may be used to indicate that, for example, a data value has changed. However, this is less preferred because it increases the probability that the user will accidentally, and possibly unknowingly, enter an incorrect data value.

Although this invention has been described above with reference to particular means, materials, and embodiments, it is to be understood that the invention is not limited to these disclosed particulars, but extends instead to all equivalents within the scope of the Description, Drawings, and following Claims.

I claim:

1. A data entry pad for a computer comprising a plurality of foot buttons, said foot buttons being configured to enter different data values according to a code of actuation of the foot buttons, the buttons being spaced-apart in a generally radial planar pattern on said pad, each of said foot buttons being distanced about 5-10 inches from the center of a heel support area also on said pad.

2. The pad of claim 1, wherein the code of actuation depends upon how long the buttons are continuously depressed.

3. The pad of claim 1, wherein the code of actuation depends upon how many times the buttons are depressed, released, and re-depressed.

4. The pad of claim 1, which comprises a cursor controller further from the heel support area than said foot buttons.

5. The pad of claim 4, which comprises a mouse control button further from the heel support area than said foot buttons.

6. The pad of claim 4, which comprises a mouse control button in the heel support area.

7. A foot key pad for a computer, which comprises a cursor controller and a mouse controller button, the cursor controller and mouse controller button being spaced-apart in a generally radial planar pattern on said pad, and both said cursor controller and said mouse controller button being distanced about 5-10 inches from the center of a heel support area also on said pad.

8. The key pad of claim 7, which comprises a plurality of mouse controller buttons.

9. The key pad of claim 8, wherein one mouse controller button is in the heel support area.

* * * * *